(12) United States Patent
Lee

(10) Patent No.: US 7,722,593 B2
(45) Date of Patent: May 25, 2010

(54) DISPOSABLE THONG UNDERWEAR

(76) Inventor: Margaret Lee, 23 Orange Ave., Irvington, NJ (US) 07111

( * ) Notice: Subject to any disclaimer, the term of this patent is extended or adjusted under 35 U.S.C. 154(b) by 0 days.

(21) Appl. No.: 11/120,219

(22) Filed: May 2, 2005

(65) Prior Publication Data

US 2005/0267438 A1 Dec. 1, 2005

Related U.S. Application Data

(60) Provisional application No. 60/574,242, filed on May 25, 2004.

(51) Int. Cl.
*A61F 13/15* (2006.01)
*A61F 13/20* (2006.01)
*A41B 9/00* (2006.01)
*A41B 9/04* (2006.01)

(52) U.S. Cl. ............... 604/396; 604/393; 604/394; 2/400; 2/406

(58) Field of Classification Search ......... 604/358–402; 2/400, 406
See application file for complete search history.

(56) References Cited

U.S. PATENT DOCUMENTS

| | | | | |
|---|---|---|---|---|
| 3,593,716 A | * | 7/1971 | Vogt | 604/366 |
| 3,608,551 A | * | 9/1971 | Seijo | 604/396 |
| 4,900,318 A | * | 2/1990 | Toth | 604/385.21 |
| 5,120,264 A | * | 6/1992 | Van Engel | 450/7 |
| 5,308,344 A | * | 5/1994 | Toth | 604/378 |
| 5,388,275 A | * | 2/1995 | Oram | 2/406 |
| 5,528,775 A | * | 6/1996 | Marenda | 2/406 |
| 5,601,545 A | * | 2/1997 | Glaug et al. | 604/385.29 |
| 5,683,373 A | * | 11/1997 | Darby | 604/385.01 |
| 5,729,835 A | * | 3/1998 | Williams | 2/406 |
| D395,504 S | * | 6/1998 | Darby | D24/125 |
| D445,181 S | * | 7/2001 | Kramer | D24/125 |
| 2003/0130643 A1 | * | 7/2003 | Drevik et al. | 604/385.31 |
| 2003/0135188 A1 | * | 7/2003 | Yoshimasa | 604/385.03 |
| 2004/0060649 A1 | * | 4/2004 | Van Gompel et al. | 156/258 |
| 2004/0064872 A1 | * | 4/2004 | Ruiter et al. | 2/400 |
| 2005/0090795 A1 | * | 4/2005 | Coleman | 604/387 |

* cited by examiner

*Primary Examiner*—Melanie J Hand
(74) *Attorney, Agent, or Firm*—Melvin K. Silverman; Yi Li

(57) ABSTRACT

A thong underpant which may be combined with a full sanitary napkin, and a method of making the same; the pad may be formed integrally with the disposable thong underpant, or the back end of the sanitary napkin affixed, as by sewing, to the stretched thong, or the front panel of the thong may be continued into the crotch region to form a partial crotch panel, just big enough to receive the adhesive on the underside of a generally rectangular sanitary napkin.

7 Claims, 4 Drawing Sheets

DISPOSABLE THONG UNDERWEAR

CROSS REFERENCE TO RELATED APPLICATIONS

This application claims priority from Provisional Patent Application No. 60/574,242, filed May 25, 2004.

FIELD OF THE INVENTION

The present invention relates to sanitary protection and disposable underwear, and especially to sanitary protection provided for thong underwear.

BACKGROUND OF THE INVENTION

Many forms of sanitary protection have been used over the years. Many years ago, women used fabric scraps to sew undergarments to wear during menstruation, sewing extra absorbent layers into the crotch portion of the undergarment. The first commercially available disposable sanitary pads were developed in about the 1920s. The sanitary pads were secured with elastic belts and/or pins. Later, sanitary pads were provided with adhesive on the underside thereof, to attach the pad to the inside surface of the crotch portion of the underwear. In recent years thong underwear has become popular. This style of underpant lacks a full crotch portion, and presents a challenge to adhering a full sanitary pad within the thong underwear.

SUMMARY OF THE INVENTION

It is an object of the present invention to provide disposable underpants with integral sanitary pads, to prevent the staining of, and eliminate the need to launder, underpants worn during menstruation. It is a further object of the present invention to provide full sanitary protection in a thong underpant construction, by permanently attaching a full sanitary pad to the stretched thong of an underpant, or by creating new thong underwear wherein the front panel is extended into the thong region of the underpant, and provides a fabric panel to which a conventional sanitary pad with adhesive strips may be attached.

These objects, as well as other objects which will become apparent from the discussion that follows, are achieved, in accordance with the present invention which comprises a disposable underpant with a unitary sanitary pad. The under pant comprises a substantially rectangular fabric panel with opposed half moon cutouts, each creating two partial side edges. Stretched elastic may be adhered to the fabric panel along the edge of the half moon cutouts, and an absorbent panel may be disposed atop the fabric panel in the crotch region, between the half moon cutouts. An impervious layer may be provided between the absorbent panel and the fabric. The absorbent panel and the impervious layer are permanently attached to the fabric panel. The opposed partial side edges, about each half moon cutout, are also joined, to complete the pant. Preferably, an elastic band is incorporated into the waist portion of the pant.

These objects will also be apparent from the following description of the present invention: a disposable thong underpant with sanitary protection formed therein, comprising a generally rectangular partial front panel having a waist portion, and elastic thong attached to the front panel opposite the waist portion, and waist bands extending from the ends of the waist portion of the front and/or back panels of thong, and being attached to the underpant so as to create a complete waistband. The underpant has a generally rectangular sanitary pad, at least a portion of the length of which lies along the thong and is permanently secured thereto when the thong is in a stretched condition.

In addition, these objects will be apparent from the following description of the present invention: a disposable thong underpants having a generally triangular partial front panel having a waist portion, and an elastic thong attached to the front panel opposite the waist portion, with sanitary protection attached to the thong. The underpant has waistbands extending from the ends of the waist portion of the panels. Along the thong, a sanitary pad is permanently secured thereto along a line of attachment, when the thong is in a stretched condition.

These objects will also be apparent for the following description of a high speed, low cost method for making the disposable thong underpant according to the present invention, comprising providing a continuous fabric layer in a first direction, providing a continuous stretched elastic band in the first direction at about the center of the width of the fabric layer, cutting away the side edges of the fabric layer to create a continuous line of thong under pants, securing the stretched elastic band to the fabric of the thong, attaching a sanitary pad to the underpant along a line of attachment securing the pad to the stretched elastic thong, and cutting the continuous line of thong underpants transversely to the first direction, to create separate underpants. The method may further include the step of securing an elastic waistband to the continuous line of under pants, transversely to the first direction.

The disposable underpants of the present invention are preferably constructed of attractive, brightly colored, patterned or solid, fabric, which may be breathable, but need not be washable. The pants may be constructed in a variety of sizes, which maybe combined with a variety of sizes or types of sanitary pads. If the number of combinations resulting form these variables is difficult to accommodate in a conventional shelf display, the pants may be easily marketed over the internet and/or available by mail.

It is anticipated that the underpants with integral sanitary pad according to the present invention will find application in hospital and medical facilities. Therefore, extra padding may be provided at the waistband for patients whose treatment results in scars or tenderness at the waist.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
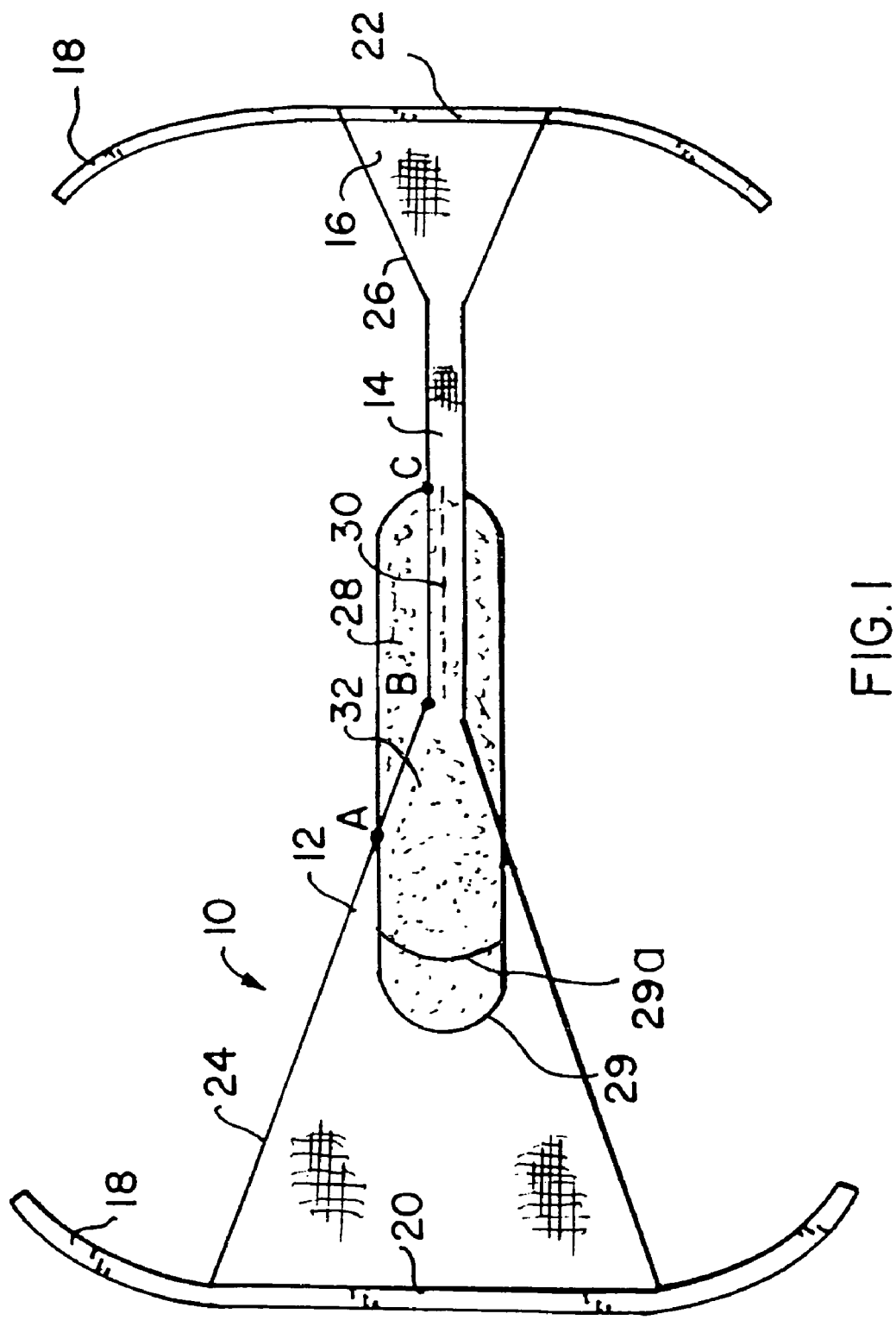
FIG. 1 is a schematic diagram of the top view of disposable thong underpant with integral sanitary pad according to the present invention.

The preferred embodiments of the present invention will now be described with reference to FIGS. 1-4 of the drawings. Identical elements in the various figures are designated with the same reference numerals.

FIG. 1 illustrates a disposable thong underpant according to the present invention, seen generally at 10, with an integral sanitary pad. The underpant comprises a partial front panel 12, attached to a thong 14, attached to a partial back panel 16. An elastic waistband 18 may be provided, and attached to the waist portion 20 of one, or both, of the front panel and back panel. The waist band is preferably elastic. If desired the partial back panel may be omitted, and the waistband extended from the front panel to the thong.

In the preferred embodiment illustrated in FIG. 1, the partial front panel, 12, comprises a triangle formed of the front waist portion and two side edges, 24. The partial back panel, 16, is also triangular in shape and comprises the back portion of the waistband, 22, and two side edges 26. A sanitary pad, 28, may be attached to the thong along a line of attachment 30. The line of attachment 30 must be created when the thong is in a stretched position. Typical thong underpants are manufactured with about 20% to about 30% elongation. As shown in FIG. 1 the line of attachment is a line of stitching. However other means, such as adhesive means, may still be used. If desired the partial front panel may be continued in the region ABC so as to underlie, and cover, the pad. As shown at 29 the front of the sanitary pad may be extended for greater absorbent capacity. Line 29a illustrates the shorter front of the traditional commercial sanitary pad. The underpant as shown generally at 10 illustrates the dimensions of the pad when the thong is in a stretched condition, such as when the sanitary pad is attached, and when the underpant is worn. In the un-stretched condition the thong may create gathering of the sanitary pad. Additionally, the line of attachment 30 may create, or may overlie, a compacted portion of the sanitary pad, with superior wicking, to move the fluid to the front and back of the pad. The line of attachment 30 predisposes the sanitary pad to fold along the line of attachment, enabling the pad to fall between the buttocks, and disposing the absorbent surface adjacent the body.

Figure 2:
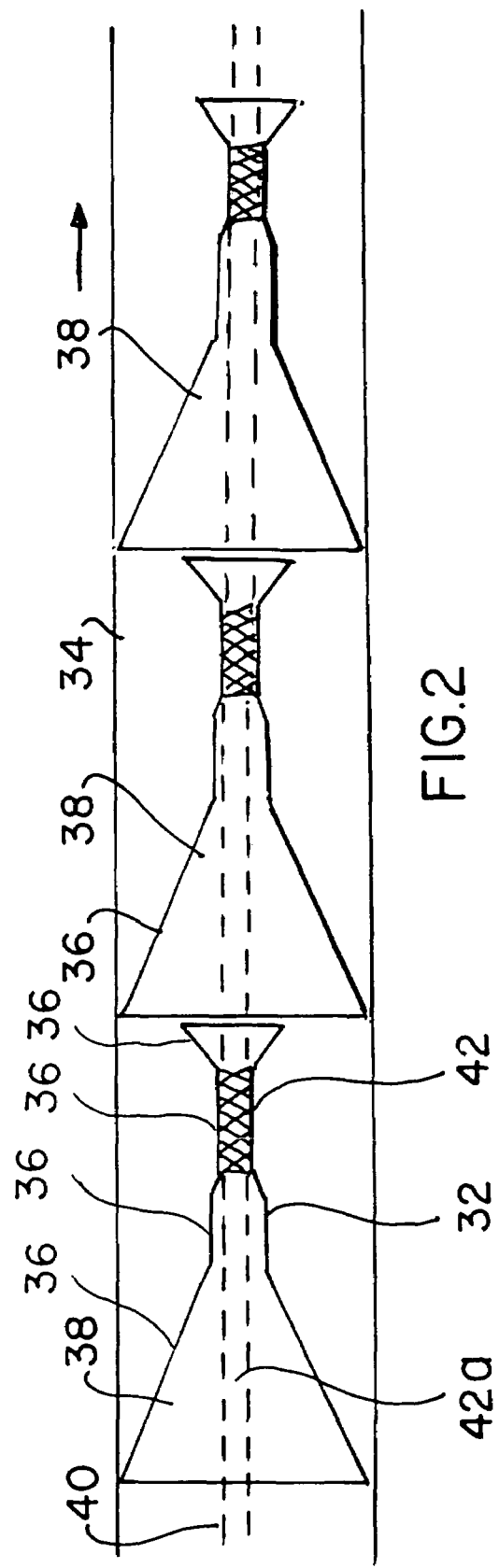
FIG. 2 is a schematic diagram of the top view of the apparatus and method for making articles according to the present invention.

FIG. 2 illustrates a method of assembly of a disposable thong underpant according to the present invention, in which the front panel is extended toward the back panel, over a portion of the thong region, to provide a fabric region, 32, to which a traditional commercial sanitary pad with lines of adhesive may be attached. FIG. 2 illustrates a continuously moving conveyor belt 34 on which the layers of material of the underpant are assembled. A continuous layer of fabric is provided atop the moving conveyor belt 34, and a stretched elastic band 40 provided in the line of direction of the conveyor belt 34, near the center of the fabric layer, and attached in discrete regions 42 to the fabric. The attachment may be by means of a hot melt adhesive, or the elastic band itself may have characteristics of an adhesive at elevated temperatures, permitting securement of the stretched elastic band to the fabric. If desired, an optional facing layer (not shown) may be secured to the fabric, such that the elastic band is disposed between the fabric and the facing layer.

In regions 42a the elastic is unsecured, and when the continuous line of articles are separated into distinct articles, cutting elastic band 40, the unsecured region 42a, the elastic band shrinks back into the article. In an alternative embodiment, the stretched elastic band 40 may be immobilized, such as by heating to melting, or to destroy its elasticity. A continuous line of interconnected articles is formed by cutting out the edges along line 36. The continuous line of interconnected articles may then be cut transversely to the direction of the conveyor belt, to yield individual articles 38 comprising disposable thong underpants, without a sanitary pad. An elastic waistband may be sewn or otherwise attached at the end edges of the articles.

Figure 3A:
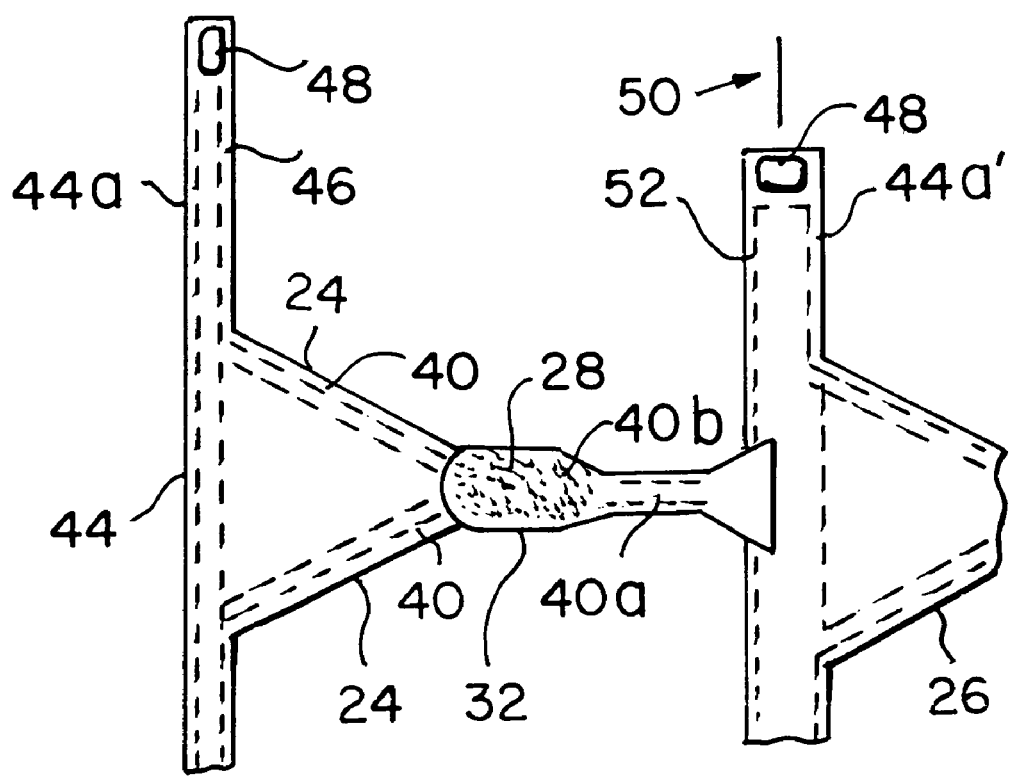
FIG. 3A is a top view of the assembly of a disposable article with elastic waistband according to the present invention

FIG. 3A illustrates the assembly of a disposable thong underpant assembled with two stretched elastic bands 40, running along the sides 24 of the front panel, and if desired, along the sides 26 of the back panel. Within the thong area, 40a, the stretched elastic bands overlap one another. Within the extended fabric region 32, the material of the elastic may be melted, as at 40b, and used to attach the sanitary pad 28, to the fabric region. As shown in FIG. 3A, underpant may be provided with a waist band 44 which may be extended, as at 44a and provided with means, such as tape tab means shown at 48, which may be used to attach the waist band to a corresponding waist band portion extending from the back panel, or directly to the back panel. A stretched elastic band 46 may be secured to the waistband to form an elasticized waistband. When the articles are cut from one another, the portion of the elastic band, which extended through the partial back panel may retract into the panel. As the articles are disposed end to end, the transverse cut, at line 50, which separates the articles, and may also cut the elastic band 52, into front and back portions, as shown in FIG. 3A.

Figure 3B:
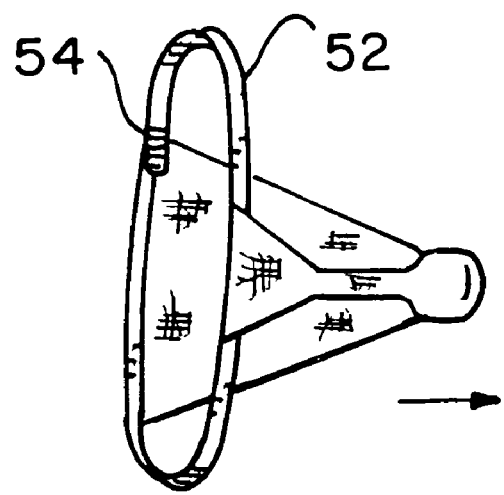
FIG. 3B is a top view of the assembly of an alternative disposable article with elastic waist according to the present invention.

FIG. 3B illustrates the assembly of an alternative construction of the underpant, provided with an elastic band 52 attached to the partial back panel in the waist portion. After the articles are separated, the back panel may be folded back to partially overly the front panel, and the ends of band 52 attached in regions 54 to the front waist portion of the front panel. The attachment may be with a separate application of hot melt or pressure sensitive adhesive, or melt bonding, or mixtures thereof.

Figure 4:
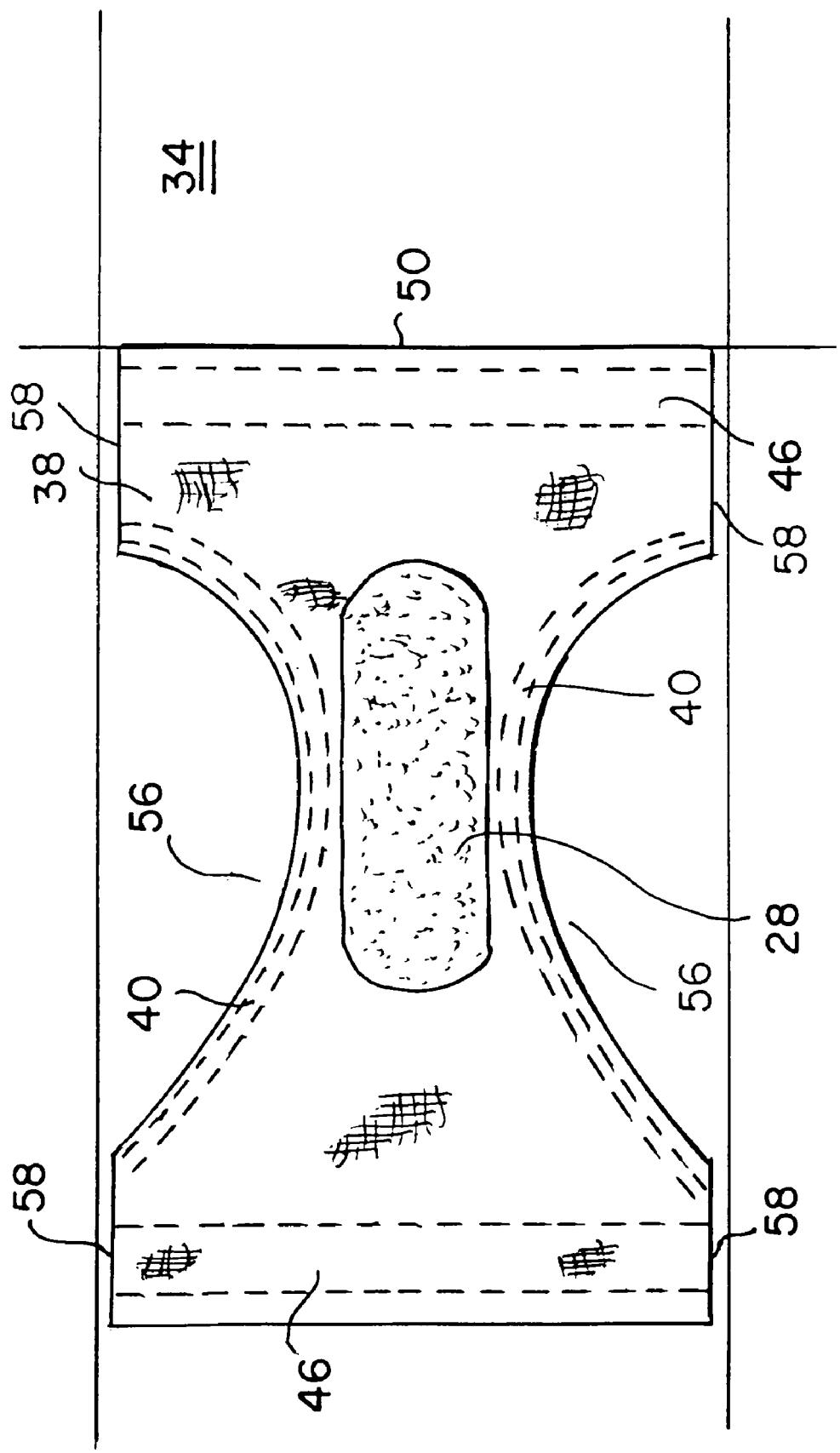
FIG. 4 is a schematic diagram of the methods of making a disposable under pant with unitary sanitary pad, according to the present invention.

FIG. 4 illustrates a continuous method for making a disposable under pant, comprising providing a fabric layer atop a conveyor belt 34, providing elastic bands 40 thereon, cutting half moon portions 56 into the side of the fabric layer, attaching a sanitary pad 28 in the crotch portion of the underpant, between the half moon cutouts 56, and securing the remaining side edges 58, and cutting the fabric layer transversely 50 to the direction of the conveyor belt, to form the underpant. As may be noted in FIG. 4, said half moon portions 56 are, more technically, parabolic in shape. If desired an elastic waistband 46 may be secured to the underpant.

There has thus been shown and described a novel disposable underwear, especially thong underpants, with a sanitary pad, and thong underwear accommodating rectangular sanitary pads, which fulfill all the objects and advantages sought therefore. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

I claim:

1. A disposable thong underwear with a sanitary pad, comprising:
   (a) a continuous fabric including a generally triangular partial front panel portion, a thong region, and a partial back panel portion;
   (b) a stretched elastic band attached to said thong region of said continuous fabric along a center of said fabric from said front panel portion to said back panel portion, forming an elastic thong portion;
   (c) an elongated absorbent sanitary pad, with at least a portion of a length thereof lying along and being permanently secured to said elastic thong portion by a line of attachment extending along a center line of said elastic thong portion when said elastic thong portion is in a stretched condition; said line of attachment predisposing said sanitary pad to fold along said line attachment, disposing an absorbent surface adjacent the body when in use; and said sanitary pad being caused gathering by said elastic thong portion when said elastic thong portion is unstretched; and
   (d) a waist band attached to waist portions of said front and back panel portions.

2. The thong underwear of claim 1, wherein said line of attachment is a line of stitching.

3. The thong underwear of claim 1, wherein said elastic band is attached to said thong region of said fabric by an adhesive.

4. The thong underwear of claim 1 further comprising stretched elastic bands secured to said sides of said front panel portion.

5. The thong underwear of claim 1 further comprising stretched elastic bands secured to said sides of said back panel portion.

6. The thong underwear of claim 1, wherein said sanitary pad further comprises regions near said edge of said pad, which wick fluid along said edge, thereby preventing a fluid from moving over said edge of said pad.

7. The thong underwear of claim 1, wherein said line of attachment creates a compacted portion of said sanitary pad, thereby moving a fluid to front and back portions of said sanitary pad.

* * * * *